United States Patent
Farley et al.

(10) Patent No.: US 6,263,248 B1
(45) Date of Patent: *Jul. 17, 2001

(54) CATHETER HAVING EXPANDABLE ELECTRODES AND ADJUSTABLE STENT

(75) Inventors: Brian E. Farley, Los Altos; Joseph M. Tartaglia, Morgan Hill, both of CA (US)

(73) Assignee: VNUS Medical Technologies, Inc., San Jose, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/394,773

(22) Filed: Sep. 10, 1999

Related U.S. Application Data

(62) Division of application No. 08/968,630, filed on Nov. 12, 1997, now Pat. No. 6,014,589.

(51) Int. Cl.[7] .................................................. A61F 7/00
(52) U.S. Cl. .............................. 607/98; 607/101; 606/32; 606/191
(58) Field of Search ................................ 606/41, 27, 32, 606/191, 194–195, 198; 607/98–102, 113

(56) References Cited

U.S. PATENT DOCUMENTS

| | | |
|---|---|---|
| 373,399 | 11/1887 | Hamilton . |
| 659,409 | 10/1900 | Mosher . |
| 833,759 | 10/1906 | Sourwine . |
| 985,865 | 3/1911 | Turner, Jr. . |

(List continued on next page.)

FOREIGN PATENT DOCUMENTS

| | | |
|---|---|---|
| 3516830 | 11/1986 | (DE) . |
| 0 189 329 A2 | 7/1986 | (EP) . |
| 0 472 368 A2 | 2/1992 | (EP) . |

(List continued on next page.)

OTHER PUBLICATIONS

Aaron, et al., Electrofulguration for Varicose Veins, The Medical Letter on Drugs and Therapeutics, Jul. 12, 1968, vol. 10, No. 14, Issue 248, p. 54.

Brunelle, et al., A Bipolar Electrode for Vascular Electrocoagulation with Alternating Current, Technical Notes, Oct. 1980, vol. 137, pp. 239–240.

Cragg et al., Endovascular Diathermic Vessel Occlusion, Diagnostic Radiology, 144: 303–308, Jul. 1982.

(List continued on next page.)

*Primary Examiner*—Linda C. M. Dvorak
*Assistant Examiner*—Roy Gibson
(74) *Attorney, Agent, or Firm*—Fulwider Patton Lee & Utecht, LLP

(57) ABSTRACT

A catheter having expandable electrodes for applying energy to a vein for a minimally invasive treatment of venous insufficiency, and having expandable stent members for limiting vein shrinkage to a final desired vein diameter. The catheter includes a set of expandable arms that are preformed into an outwardly bowed configuration. An electrode is mounted on each arm. When uncovered by sliding a control sleeve proximally, the electrode arms expand outwardly into apposition with the vein wall for applying energy to the vein wall to heat and shrink the vein. The catheter further includes a set of expandable stent arms deployed to the final desired diameter of the vein. The electrode arms and the stent arms are decoupled so that each is separately controllable. In a method, the stent arms are expanded outward to the desired final diameter of the vein. The electrode arms are then expanded into apposition with the vein wall and energy is applied to shrink the vein into contact with the stent arms. The application of energy is ceased at that time.

12 Claims, 8 Drawing Sheets

U.S. PATENT DOCUMENTS

| | | |
|---|---|---|
| 3,230,957 | 1/1966 | Seifert . |
| 3,301,258 | 1/1967 | Werner et al. . |
| 3,557,794 | 1/1971 | Van Patten . |
| 3,920,021 | 11/1975 | Hiltebrandt . |
| 4,016,886 | 4/1977 | Doss et al. . |
| 4,043,338 | 8/1977 | Homm et al. . |
| 4,119,102 | 10/1978 | LeVeen . |
| 4,154,246 | 5/1979 | LeVeen . |
| 4,312,364 | 1/1982 | Convert et al. . |
| 4,346,715 | 8/1982 | Gammell . |
| 4,522,205 | 6/1985 | Taylor et al. . |
| 4,643,186 | 2/1987 | Rosen et al. . |
| 4,660,571 | 4/1987 | Hess et al. . |
| 4,664,120 | 5/1987 | Hess . |
| 4,699,147 | 10/1987 | Chilson et al. . |
| 4,709,698 | 12/1987 | Johnston et al. . |
| 4,765,331 | 8/1988 | Petruzzi et al. . |
| 4,776,349 | 10/1988 | Nashef et al. . |
| 4,807,620 | 2/1989 | Strul et al. . |
| 4,823,812 | 4/1989 | Eshel et al. . |
| 4,945,912 | 8/1990 | Langberg . |
| 4,966,597 | 10/1990 | Cosman . |
| 4,976,711 | 12/1990 | Parins et al. . |
| 4,979,948 | 12/1990 | Geddes et al. . |
| 5,010,894 | 4/1991 | Edhag . |
| 5,057,107 | 10/1991 | Parins et al. . |
| 5,078,717 | 1/1992 | Parins et al. . |
| 5,100,423 | 3/1992 | Fearnot . |
| 5,117,828 | 6/1992 | Metzger et al. . |
| 5,122,137 | 6/1992 | Lennox . |
| 5,156,151 | 10/1992 | Imran . |
| 5,188,602 * | 2/1993 | Nichols ............................... 604/113 |
| 5,215,103 | 6/1993 | Desai . |
| 5,255,678 | 10/1993 | Deslauriers et al. . |
| 5,263,493 | 11/1993 | Avitall . |
| 5,275,610 | 1/1994 | Eberbach . |
| 5,282,845 | 2/1994 | Bush . |
| 5,293,869 | 3/1994 | Edwards et al. . |
| 5,313,943 | 5/1994 | Houser et al. . |
| 5,383,917 | 1/1995 | Desai et al. . |
| 5,397,339 | 3/1995 | Desai . |
| 5,405,322 | 4/1995 | Lennox et al. . |
| 5,409,000 | 4/1995 | Imran . |
| 5,411,025 | 5/1995 | Webster, Jr. . |
| 5,423,815 | 6/1995 | Fugo . |
| 5,437,664 | 8/1995 | Cohen et al. . |
| 5,449,381 | 9/1995 | Imran . |
| 5,458,596 | 10/1995 | Lax et al. . |
| 5,465,717 | 11/1995 | Imran et al. . |
| 5,472,441 | 12/1995 | Edwards et al. . |
| 5,505,730 | 4/1996 | Edwards . |
| 5,514,130 | 5/1996 | Baker . |
| 5,545,161 | 8/1996 | Imran . |
| 5,556,396 | 9/1996 | Cohen et al. . |
| 5,709,224 | 1/1998 | Behl et al. . |
| 5,779,698 | 7/1998 | Clayman et al. . |
| 5,810,804 | 9/1998 | Gough et al. . |
| 5,817,092 | 10/1998 | Behl . |
| 5,827,268 | 10/1998 | Laufer . |
| 5,863,290 | 1/1999 | Gough et al. . |
| 5,868,740 | 2/1999 | LeVeen et al. . |
| 5,916,235 | 6/1999 | Guglielmi . |
| 6,071,277 * | 6/2000 | Farley et al. ............................ 606/27 |

FOREIGN PATENT DOCUMENTS

| | | |
|---|---|---|
| 0 629 382 A1 | 12/1994 | (EP) . |
| 0 738 501 A1 | 10/1996 | (EP) . |
| 2 271 932 | 5/1994 | (GB) . |
| WO 91/01773 | 2/1991 | (WO) . |
| WO 92/12681 | 8/1992 | (WO) . |
| WO 93/21846 | 11/1993 | (WO) . |
| WO 94/07446 | 4/1994 | (WO) . |
| WO 94/21170 | 9/1994 | (WO) . |
| WO 95/02370 | 1/1995 | (WO) . |
| WO 95/10236 | 4/1995 | (WO) . |
| WO 95/10322 | 4/1995 | (WO) . |
| WO 95/31142 | 11/1995 | (WO) . |
| WO 96/32885 | 10/1996 | (WO) . |
| WO 97/17892 | 5/1997 | (WO) . |
| WO 97/32532 | 9/1997 | (WO) . |
| WO 98/55072 | 12/1998 | (WO) . |

OTHER PUBLICATIONS

Crockett, Don, Jr., M.D. et al., Preliminary Experience with an Endovascular Catheter for Electrocoagulation of Peripheral Veins, The Journal of Vascular Technology, Winter 1996, at 19–22.

Gradman, Venoscopic Obliteration of Variceal Tributaries Using Monopolar Electrocautery, Journal of Dermatology Surgery Oncology, 1994, 20, p. 482–485.

Inturri, Pathophysiology of Portal Hypertension, Journal of Vascular Technology 19 (5–6):271–276, Sep.–Dec. 1995.

Money, Samuel R. M.D., Endovascular Electroablation of Peripheral Veins, 22 Annual Symposium, Current Critical Problems, New Horizons and Techniques in Vascular and Endovascular Surgery (Nov. 1995).

Ogawa, et al., Electrothrombosis As a Treatment of Cirsoid Angioma in the Face and Scalp and Varicosis of the Leg, Technical Notes, No. 3, Oct., pp. 310–311.

O'Reilly, Kevin, A Technique of Diathermy Sclerosis of Varicose Veins, The Australian, New Zealand Journal of Surgery, vol. 51, No. 4, Aug. 1981, pp. 379–382.

O'Reilly, Kevin, Endovenous Diathermy Sclerosis AE a Unit of the Armamentarium for the Attack on Varicose Veins, The Medical Journal of Australia, Jun. 1, 1974, at 900.

Watts, G.T., Endovenous Diathermy Destruction of Internal Saphenous, British Medical Journal, Oct. 7, 1972, p. 53.

O'Reilly, Kevin, Endovenous Diathermy Sclerosis of Varicose Veins, The Australian, New Zealand Journal of Surgery, vol. 47, No. 3, Jun. 1977, pp. 393–395.

* cited by examiner

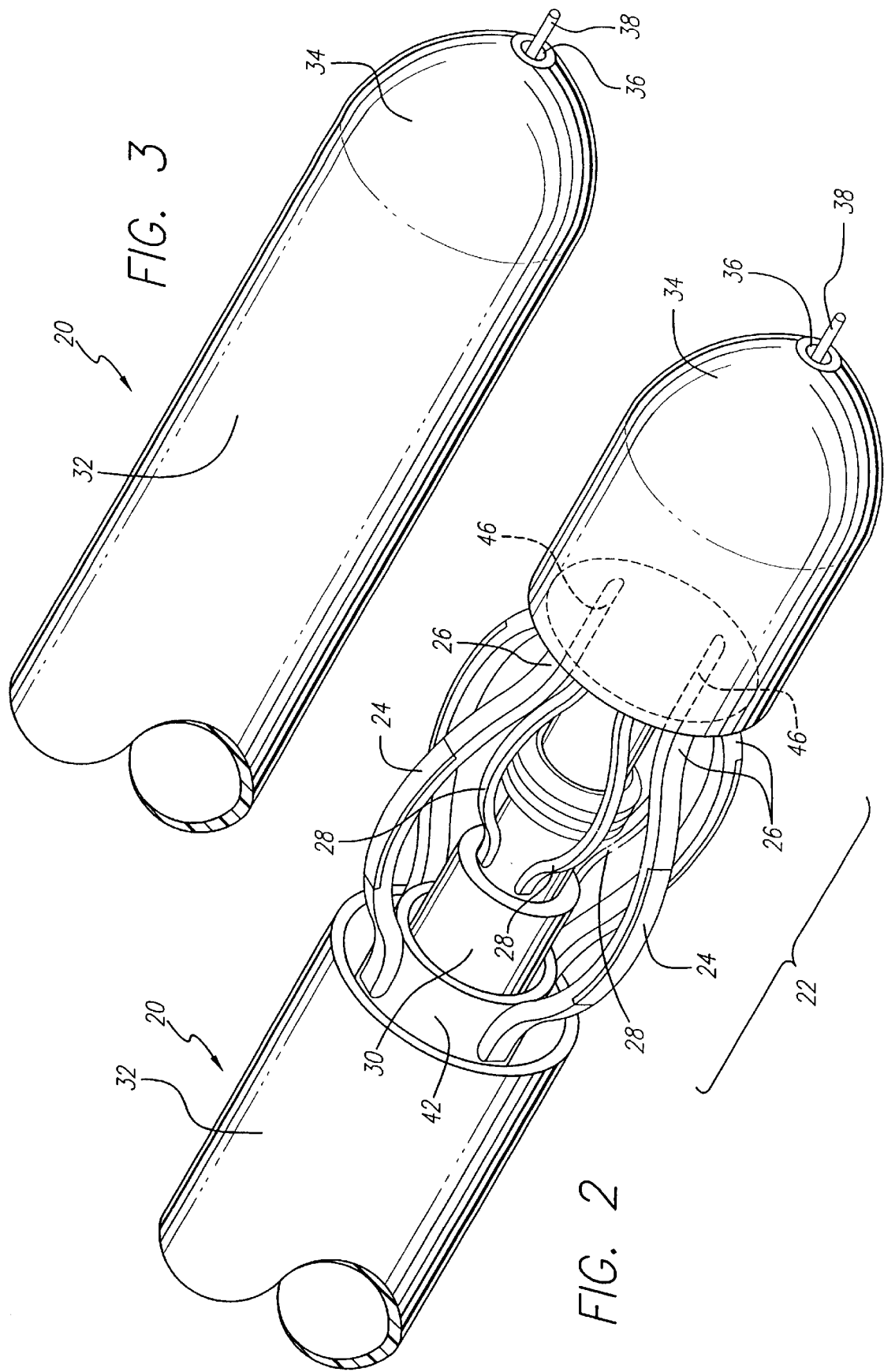

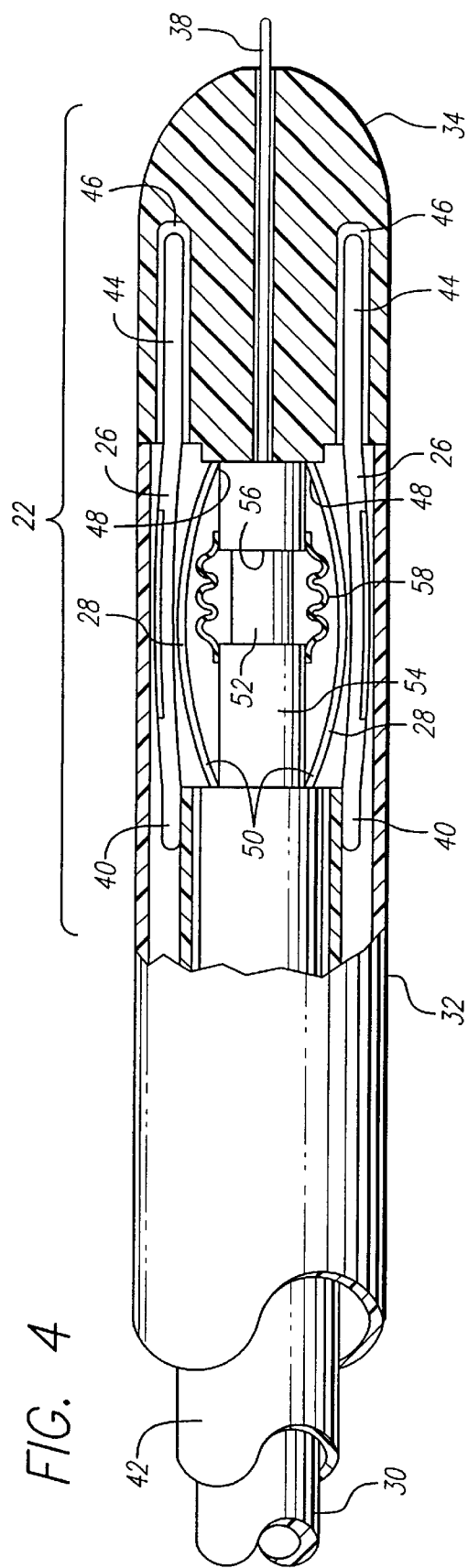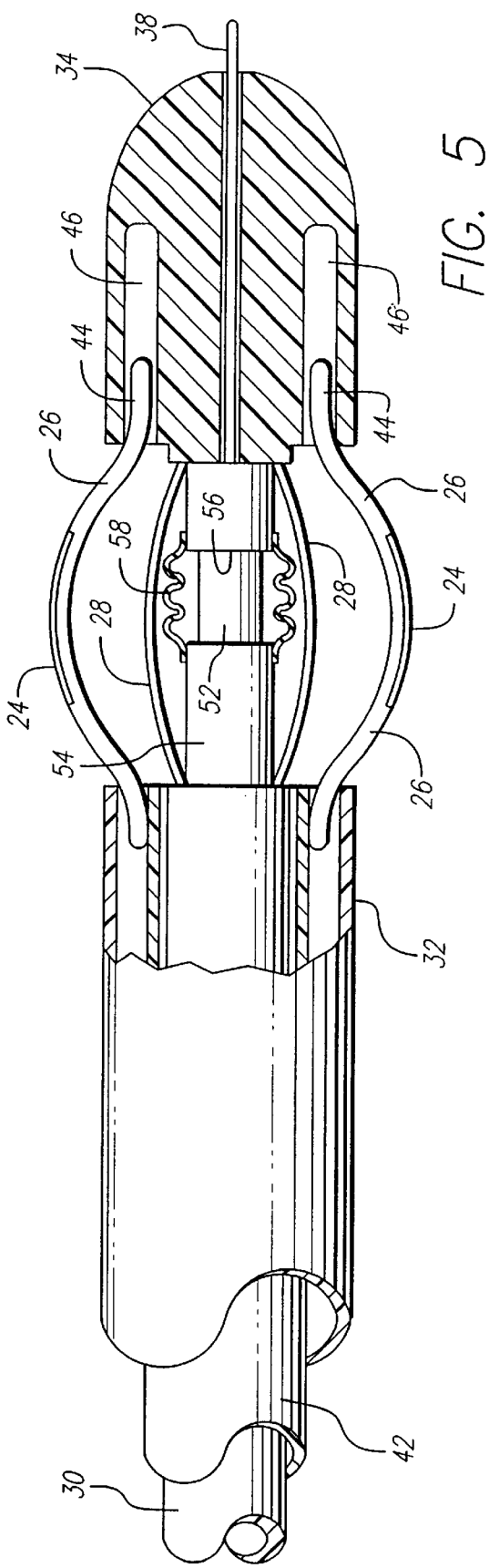

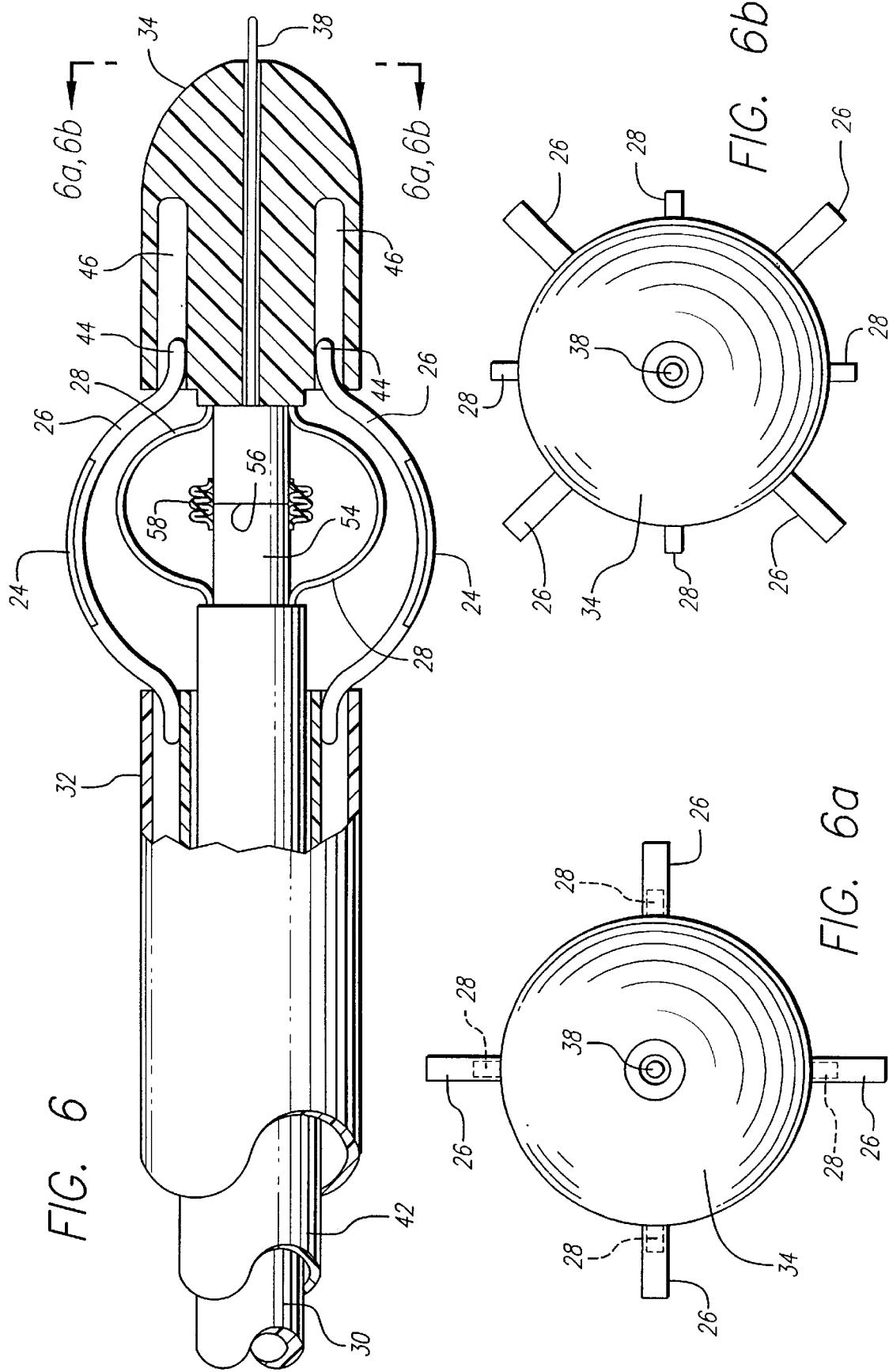

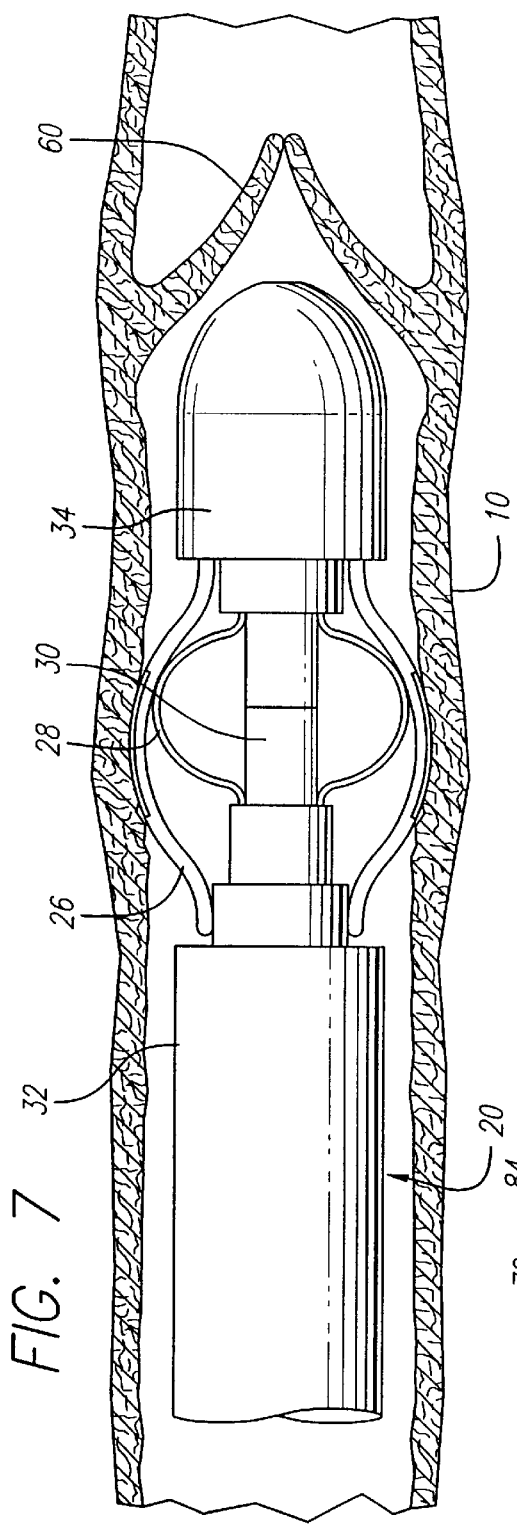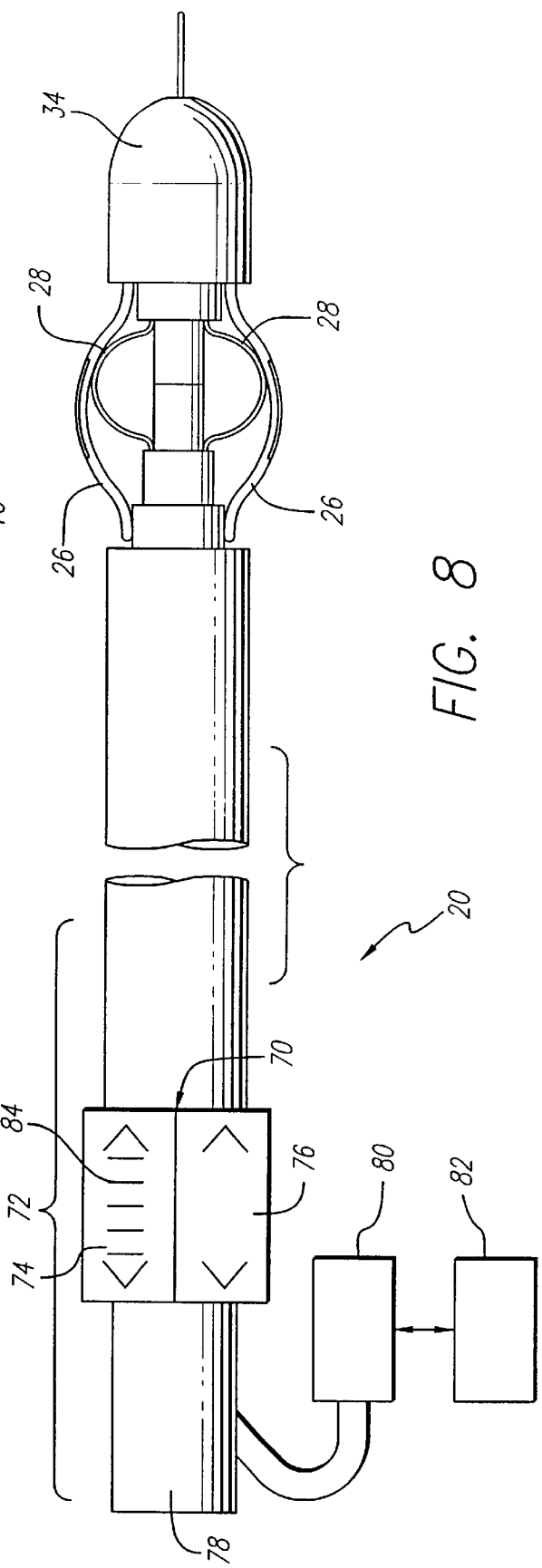
FIG. 7
FIG. 8

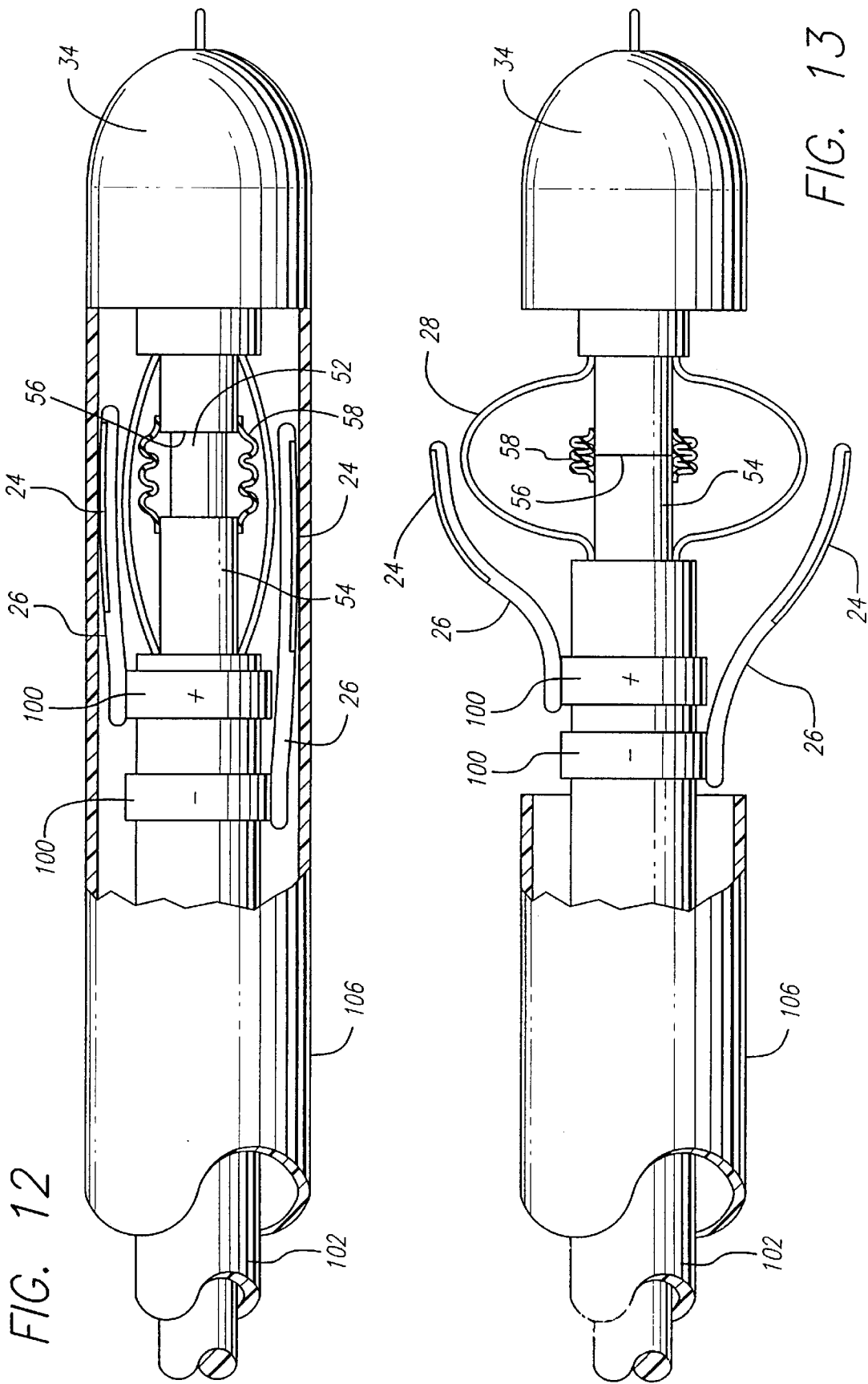

US 6,263,248 B1

CATHETER HAVING EXPANDABLE ELECTRODES AND ADJUSTABLE STENT

This application is a divisional of Ser. No. 08/968,630 filed Nov. 12, 1997, now U.S. Pat. No. 6,014,589.

BACKGROUND OF THE INVENTION

The invention relates generally to the controlled shrinkage of biological tissue, and more particularly, to a minimally invasive apparatus and method using a catheter-based system having an energy-delivery arrangement for providing energy to shrink the biological tissue while having a mechanical limiting device for controlling the shrinkage.

The human venous system of the lower limbs consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

The venous systems contain numerous one-way valves for directing blood flow back to the heart. Venous valves are usually bicuspid valves, with each cusp forming a sack or reservoir for blood which, under retrograde blood pressure, forces the free surfaces of the cusps together to prevent retrograde flow of the blood and allows only antegrade blood flow to the heart. When an incompetent valve is in the flow path, the valve is unable to close because the cusps do not form a proper seal and retrograde flow of blood cannot be stopped.

Incompetence in the venous system can result from vein dilation, such as that shown in FIG. 1. In FIG. 1 there is shown a partial cross-sectional view of a partially dilated vein 10 from a lower limb having incompetent valves 12. These veins are often disposed within muscle tissue. Veins have bicuspid valves, and in a normal and competent valve 14, each cusp forms a sack or reservoir 16 for blood which, under pressure, forces the free edges of the cusps together to prevent retrograde flow of the blood and allow only antegrade flow to the heart. The arrow 18 leading out the top of the vein represents the antegrade flow of blood back to the heart. Properly operating venous valves prevent retrograde flow as blood is pushed forward through the vein lumen and back to the heart.

When an incompetent valve 12 such as those shown in the lower part of the vein, encounters retrograde flow, the cusps of the valve do not seal properly, the valve is unable to close, and retrograde flow of blood may occur. As the valves fail, increased pressure is imposed on the lower veins and the lower valves of the vein, which in turn exacerbates the failure of these lower valves. The stretching of dilated veins may result in incompetent valves. The valve cusps can experience separation at the commissures due to the thinning and stretching of the vein walls at those points. Valves can also become incompetent as a result of loose, floppy valve leaflets that can prolapse in response to retrograde blood flow or high proximal venous pressure. Loose leaflets of the venous valve results in redundancy which allows the leaflets to fold on themselves and leave the valve open. When the venous valve fails, there is an increased strain and pressure on the lower venous sections and overlying tissues, sometimes leading to additional valvular failure. Two venous conditions which often involve vein dilation are varicose veins and more symptomatic chronic venous insufficiency.

The varicose vein condition includes dilation and tortuosity of the superficial veins of the lower limbs, resulting in unsightly discoloration, pain, swelling, and possibly ulceration. Varicose veins often involve incompetence of one or more venous valves, which allow reflux of blood within the superficial system. This can also worsen deep venous reflux and perforator reflux. Current treatments include surgical procedures such as vein stripping, ligation, and occasionally, vein segment transplant, venous valvuloplasty, and the implantation of various prosthetic devices. The removal of varicose veins from the body can be a tedious, time-consuming procedure having a painful and slow healing process. In addition, patients with varicose veins may undergo injection sclerotherapy, or removal of vein segments. Complications, scarring, and the loss of the vein for future cardiac and other by-pass procedures may also result. Along with the complications and risks of invasive surgery, varicose veins may persist or recur, particularly when the valvular problem is not corrected. Due to the long, technically demanding nature of the surgical valve reconstruction procedure, treating multiple venous sections with surgical venous valve repair is rarely performed. Thus, a complete treatment of all important incompetent valves has been impractical.

Non-obstructive chronic venous insufficiency (CVI) is a problem caused by degenerative weakness in the vein valve segment, or by hydrodynamic forces acting on the tissues of the body, especially the legs, ankles and feet. As the valves in the veins fail, the hydrostatic pressure increases on the next venous valves down, causing those veins to dilate. As this continues, more venous valves will eventually fail. As they fail, the effective height of the column of blood above the feet and ankles grows, and the weight and hydrostatic pressure exerted on the tissues of the ankle and foot increases. When the weight of that column reaches a critical point as a result of the valve failures, ulcerations of the ankle begin to form, which start deep and eventually come to the surface. These ulcerations do not heal easily because of poor venous circulation due to valvular incompetence in the deep venous system and other vein systems.

Chronic venous insufficiency often consists of hypertension of the lower limb in the deep, perforating and often superficial veins, and may result in discoloration, pain, swelling and ulceration. Existing treatments for chronic venous insufficiency are often less than ideal. These treatments include the elevation of the legs, compressing the veins externally with elastic support hose, perforator ligation, surgical valve repair, and grafting vein sections with healthy valves from the arm into the leg. These methods have variable effectiveness. Moreover, invasive surgery has its associated complications with risk to life and expense. Similarly, the palliative therapies require major lifestyle changes for the patient. For example, the ulcers may recur unless the patient continues to elevate the legs and use pressure gradient stockings for long continuous periods of time.

Due to the time-consuming and invasive nature of the current surgical treatments, such as valvuloplasty or vein segment grafting, typically only one valve is treated during any single procedure. This greatly limits the ability of the physician to fully treat patients suffering from chronic venous insufficiency. Every instance of invasive surgery, however, has its associated complications with morbidity and expense.

Another type of treatment, the ligation of vascular lumina by cauterization or coagulation using electrical energy from an electrode, has been employed as an alternative to the surgical removal of superficial and perforator veins. However, such ligation procedures also close off the lumen, essentially destroying its functional capability. For example, it is known to introduce an electrode into the leg of a patient, and position the electrode adjacent the exterior of the varicose vein to be treated. Through a small stab incision, a probe is forced through the subcutaneous layer between the fascia and the skin, and then to the vein to be destroyed. A monopolar electrode at the outer end of the probe is placed adjacent the varicose vein and the return electrode is placed on the skin. Once properly positioned, an alternating current of 500 KHz is applied to destroy the adjacent varicose vein by electrocoagulation. The coagulated vein loses the function of allowing blood to flow through, and is no longer of use. For example, occluding or ligating the saphenous vein would render that vein unavailable for harvesting in other surgical procedures such as coronary by-pass operations.

In a catheter for treatment of dilated veins by providing RF or other energy to the vein tissue, expandable electrodes have been brought into contact with the vein, energy has been applied to the vein through the electrodes, and as the vein shrinks due to the heat generated, the electrodes are contracted to the final desired vein diameter. Such expandable electrodes, however can be difficult to precisely adjust to keep them in contact with the vein wall as it shrinks. Contracting the electrodes too rapidly removes them from apposition with the vein wall and energy will no longer be imparted. Shrinkage of the vein wall may then cease. It is also difficult to set the final desired vein diameter with the expandable electrodes as it is sometimes difficult to visualize the electrode positions with ultrasound, especially when the electrodes are contracting in diameter.

Hence, those skilled in the art have recognized a need for an expandable electrode catheter for shrinking biological tissue by applying energy to that tissue with a set of energy application elements while limiting the final diameter of the shrinking tissue with a different device. A further need has been recognized for such an expandable electrode catheter to maintain intimate contact between the vessel wall and the electrodes, while avoiding the need to maintain precise control over the electrodes. The invention fulfills these needs and others.

SUMMARY OF THE INVENTION

Briefly, and in general terms, the present invention provides a minimally invasive apparatus and method for controllably shrinking biological tissue to a predetermined size by applying energy to the tissue with electrodes and controlling the shrinkage of the tissue with an adjustable and removable stent.

In one aspect of the present invention, an apparatus includes two expandable elements. A first comprises an expandable electrode expanded to apply energy to the biological tissue to shrink the tissue to a predetermined desired final diameter. The second comprises an adjustable stent device that is adjusted to the desired diameter to which the tissue is to be shrunk and which prevents the tissue from shrinking to a diameter less than the stent diameter.

Another aspect of the present invention is to provide an apparatus wherein the expandable electrodes and the adjustable stent are decoupled from one another such that they may be independently controlled.

In a further aspect, the expandable energy application device is biased outwardly to automatically come into apposition with the biological tissue. Further, the expandable energy application device is mounted at a first end to the catheter and is free to move at a second end wherein as the tissue shrinks, the tissue tends to force the expandable energy application device to contract and the second end moves freely to permit the expandable energy application device to contract inward. In a more detailed aspect, the catheter further includes a first actuation device controllable from the proximal end of the catheter disposed to contract the expandable energy application device when the first actuation device is moved in one direction and to release the expandable energy application device to permit the expansion of the expandable energy application device into apposition with the tissue when the first actuation device is moved in another direction. In a further aspect, the expandable energy application device is mounted in a cantilevered fashion to the catheter.

In yet another aspect in accordance with the invention, the expandable energy application device comprises a plurality of flexible arms each of which is pre-formed into an outwardly bowed configuration with an electrode mounted on the arm for apposition with the tissue. The first slidable actuation sleeve is disposed so as to contract the flexible arms when slid in one direction and to release the flexible arms to permit the expansion of the arms into apposition with the tissue when slid in another direction.

In another aspect, a stent control device is coupled between the proximal end of the catheter and the stent device to adjust the expansion of the stent device to the predetermined size, wherein the adjustable stent device comprises an expandable stent arm controllable by the stent control device to bow outwardly from the working end to the predetermined distance. In a more detailed aspect, the stent control device comprises a second slidable actuation sleeve disposed to contract the stent device when slid in one direction and to expand the stent device outwardly when slid in another direction.

In further aspects, the stent device comprises a plurality of expandable stent arms having strengths selected so that said arms will stop further shrinkage of the tissue once the tissue has come into contact with the arms. Further, the stent control device comprises a sleeve connected to one end of the stent arms, the movement of the sleeve controlling the expansion and contraction of the stent arms.

In another aspect of the invention, the plurality of stent devices are overlayed by the plurality of expandable flexible arms having electrodes. In yet another aspect, the plurality of stent devices are interspaced with the plurality of expandable flexible arms.

In yet another aspect in accordance with the invention, the catheter comprises a handle at its proximal end having gradation indications wherein the position of the second activation device is indicated by the gradations which also indicate the amount of expansion of the stent arms.

These and other aspects and advantages of the present invention will become apparent from the following more detailed description, when taken in conjunction with the accompanying drawings which illustrate, by way of example, the preferred embodiments of the invention.

BRIEF DESCRIPTION OF THE DRAWINGS

FIG. 2 is a perspective view of an RF energy delivery system in accordance with aspects of the invention using a catheter having expandable electrodes for imparting energy to the wall of a vein and having an adjustable stent device for limiting the vein shrinkage. In this view, both the electrode arms and the stent device arms have been shown expanded outwardly;

FIG. 3 is a view of the catheter of FIG. 2 with the outer sleeve moved to the extreme distal position thereby covering the electrode and stent device arms;

FIG. 4 is a partial cross-section view of the catheter shown in FIG. 3 with the outer sleeve moved to the extreme distal position thereby covering the electrode and stent device arms;

FIG. 5 is a partial cross-section view of the catheter of FIG. 2 showing expansion of the electrode arms but showing the stent arms in the contracted position;

FIG. 6 is a partial cross-section view of the catheter of FIG. 2 showing expansion of both the electrode arms and the stent arms for an operational configuration for applying energy to a vein wall and for mechanically limiting the amount of shrinkage of the vein;

FIG. 6a is an end view of the catheter taken along line 6a—6a of FIG. 6 depicting a configuration in which the electrode arms overlay the stent arms;

FIG. 6b is an end view of the catheter taken along line 6b—6b of FIG. 6 depicting a configuration in which the electrode arms are interspaced between the stent arms;

FIG. 7 is a view of the catheter of FIG. 6 in an antegrade position in a vein after energy has been applied to the vein and it has shrunk to a predetermined inner diameter showing the electrode arms having been contracted to the diameter of the stent device by the shrinkage of the vein wall;

FIG. 8 is a system view of the catheter of FIG. 2 showing a proximal end of the catheter with a control handle and connections to a power generator, processor control, and a guide wire or fluid flush entry port;

FIG. 12 is an alternate embodiment similar to that shown in FIG. 10 but with cantilevered electrode arms, showing those arms in the restricted position; and FIG. 13 is the same embodiment as shown in FIG. 12 but with the cantilevered arms in the expanded position.

DETAILED DESCRIPTION OF THE PREFERRED EMBODIMENTS

Figure 1:
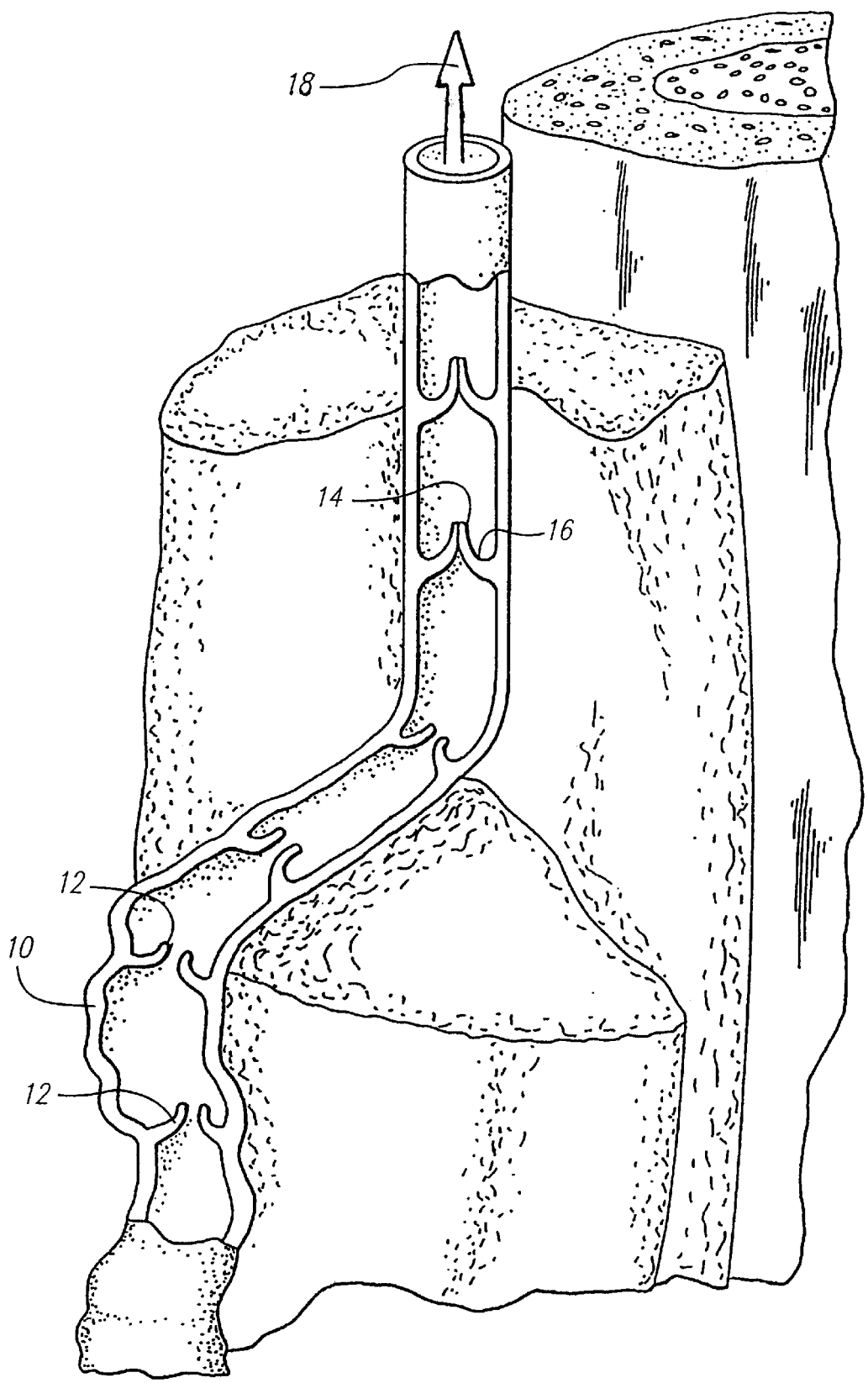
FIG. 1 is a cross-section view of venous insufficiency in a lower limb showing both dilation of the vein and multiple incompetent valves which are to be treated in accordance with the present invention.

Referring now to the drawings wherein like reference numerals designate like or corresponding elements among the several views, there is shown in FIG. 2 a catheter 20 having a working end 22 for delivering electrodes 24 to a venous treatment site, such as that shown in FIG. 1. The electrodes 24 provide RF energy at the working end 22 of the catheter 20 to heat and shrink venous tissue between the electrodes 24. The working end 22 includes a plurality of expandable electrode arms 26 on which the electrodes 24 are mounted. Also shown is an adjustable stent device comprising a plurality of expandable stent arms 28 that can be expanded outward to mechanically limit shrinkage of the vein. In this embodiment, there are four electrode arms 26 although only three can be seen, each of which includes an electrode 24, and there are four stent arms 28, also only three of which can be seen. Each of the arms is expandable outwardly, although the mechanisms controlling this expansion differ.

In the embodiment of FIG. 2, the electrode arms are pre-formed into an outwardly bowed shape, such as that shown. The arms may be formed of a material retaining that shape and which will return to that shape after being forced to assume a flattened shape. They are thus biased outward. Two examples of such a material are spring steel, and the shape memory material known as Nitinol™. To form the electrodes on the metallic arms, insulation on the arms is removed at the electrode site thus exposing the underlying metal for transferring electrical energy. Other means of forming an electrode may be used such as separately mounting an electrode to non-metallic arms. The electrodes 24 may be formed by cutting the insulating material away with a laser or razor blade, for example.

Other biocompatible materials may be used for the electrode arms 26 and electrodes 24 but in this case, the electrode arms 26 are biased outwardly to the expanded position by pre-forming them in the outwardly bowed configuration shown in FIG. 2. The electrode arms 26 in one embodiment comprise flat metallic strips that provide good contact with the vessel wall. The electrodes 24 also comprise strips that have relatively large flat surfaces for contacting the vein wall. Such flat strips can have widths ranging from 0.127 to 1.270 mm (0.005 to 0.050 in.), and preferably between 0.381 to 0.762 mm (0.015 and 0.030 in.), to allow four or more electrodes around the catheter shaft. The flat strips are thin enough to exhibit minimal dilating force on the vein. Rounded wires may also be used with a diameter preferably between about 0.120 to 0.350 mm (0.005 to 0.015 in), but can be up to about 0.700 mm (0.030 in). In another embodiment, the surface of the electrode that contacts the vein wall is curved which may assist in obtaining greater contact with the rounded contour of the vein wall. In one embodiment, the electrode surface is hemispherical in shape. In another, the electrode resembles a hemisphere but is hollowed such that it is convex on its outer shape facing the vein wall and is concave on its inner shape that faces the center of the vein.

The insulation over the electrode arms 26 can be polyimide, paralyene, PET, polyurethane, or another type of insulating film that may be extruded onto the electrode. The insulation layer is typically 0.013 mm (0.001 in.) thick and covers both sides and all edges of the electrode arms 26. The insulation provided along the inner radius of the electrode arms 26 away from the venous tissue further prevents heating the blood flowing in the vein and reduces the likelihood of coagulation. The remaining exposed area of the electrode arms 26 is the electrode 24 and is preferably the area which contacts the venous tissue during apposition. The heating effect is then focused along that portion of the venous tissue and between positive and negative electrodes. Where the electrode arms 26 are rectangularly shaped, the electrode area 24 that act as the electrode would then occupy only one face of that arm. The insulation surrounding the arm can further cover the peripheral edges of the exposed face of the arm to further isolate the blood flow from unintended heating effects. The expandable electrode arms 26 were made long enough in one embodiment to expand outwardly to treat veins up to fifteen mm in diameter.

The working end 22 of the catheter 20 shown in FIG. 2 also includes expandable stent arms 28 that provide a mechanical limit to the amount of shrinkage that can be incurred as a result of heating the vein wall. These stent arms 28 are connected at their distal ends to the distal end of the catheter and at their proximal ends to a stent actuation sleeve 30. Sliding the stent actuation sleeve 30 in the distal direction results in the stent arms 28 being forced to expand outwardly as shown in FIG. 2. Sliding the stent actuation sleeve 30 in the proximal direction will cause the stent arms 28 to contract inwardly towards the shaft of the catheter at the working end. However, movement of the stent actuation sleeve 30 does not affect the expansion or contraction of the electrode arms 26.

Control over the electrode arms 26 in the embodiment shown in FIGS. 2 and 3 is accomplished by sliding movement of the electrode actuation sleeve 32. Sliding the electrode actuation sleeve 32 in the proximal direction as shown in FIG. 2 frees the electrode arms 26 allowing them to assume their pre-formed outwardly bowed shape, as also shown in FIG. 2. Sliding the electrode actuation sleeve 32 in the distal direction as shown in FIG. 3 covers the electrode arms 26 causing them to contract towards the catheter shaft. However, the stent arms and the electrode arms are decoupled from each other.

The catheter 20 also includes a guide wire lumen (not shown) and the working end 22 includes a distal tip 34 with a guide wire port 36 through which a guide wire 38 may be advanced into the vasculature of the patient. The catheter tip 34 and the tip of the guide wire 38 are preferably rounded. The guide wire lumen is preferably insulated so as to prevent or minimize any coupling effect the electrodes 24 may have on the guide wire 38. The guide wire 38 can be removed before the application of RF energy to the electrodes 24. The guide wire lumen can also allow for the delivery or perfusion of medicant and cooling solution to the treatment area during application of the RF energy.

The distal tip 34 is shown to have a nosecone shape, but can have other shapes that allow tracking of the catheter 20 over the guide wire 38 and through bends in the venous system. The nosecone-shaped tip 34 can be fabricated from a polymer having a soft durometer, such as 44 Shore A. Alternatively, the tip 34 can be constructed from a spring covered with a thin layer of polyethylene shrink tubing.

Referring now to the more detailed drawings of FIGS. 4, 5, and 6, the working end 22 of the catheter of FIGS. 2 and 3 is shown in partial cross-section view. FIG. 4 presents the working end of the catheter in the case where both the electrode arms 26 and the stent arms 28 are in contracted positions as shown in perspective view in FIG. 3. The stent actuation sleeve 30 has been moved to the proximal position and the electrode actuation sleeve 32 has been moved to the distal position to contract the respective arms. In this configuration, the catheter 20 may be introduced and advanced to the treatment site, or may be removed therefrom.

The electrode arms 26 are attached at their proximal ends 40 to a first support tube 42 that remains immobile. The distal ends 44 of the electrode arms 26 are free to move within slots 46 formed in the distal tip 34 of the catheter 20. As the electrode actuation sleeve 32 is moved distally to cover the electrode arms 26, the arms contract towards the shaft of the catheter and their distal ends 44 move in the distal direction farther into the slots 46. This arrangement allows for free movement of the electrode arms. Because the electrode arms 26 are attached at their proximal ends 40 and they are bowed outwardly, the electrode actuation sleeve 32 may be easily slid distally to contract the electrode arms 26.

In FIG. 4, the stent arms 28 are also shown in the contracted position. The stent arms are firmly attached at their distal ends 48 to the distal tip 34 of the catheter and at their proximal ends 50 to the stent actuation sleeve 30. Because the distal tip 34 is held in position in relation to the catheter shaft but the stent actuation sleeve 30 is movable in relation to the same shaft, moving the stent actuation shaft 30 distally will force the stent arms 28 to bow outwardly in accordance with the amount of movement of the stent actuation sleeve 30. Conversely, moving the stent actuation sleeve 30 proximally will cause the stent arms 28 to contract.

In the operation of the stent arms 28, an inner catheter shaft 52 extends the entire length of the catheter and connects the distal tip 34 to the proximal end of the catheter. The proximal ends 50 of the stent arms 28 are connected to the stent actuation sleeve 30 that is coupled to an inner stop tube 54 that slides over the inner shaft 52 with the stent actuation sleeve 30. A stop surface 56 is coupled to the distal tip 34 and provides a hard stop against further distal movement of the stent actuation sleeve 30. Its operation is shown and described further in relation to FIG. 6. A bellows 58 surrounds the moving tubes and prevents the seepage of blood and other fluids into the catheter past the moving parts.

The bellows 58 is typically a shrink-tube membrane; its ends are secured onto the inner stop tube 54 and the stop surface 56. The bellows 58 prevents fluid from getting between the shafts of the catheter. The central area of the bellows 58 is not sealed down and folds up when the sliding motion of the inner stop tube 54 over the inner shaft 52 expands and contracts the stent arms 28. The bellows 58 may be blown in a mold or free-blown for initial expansion, and may be heat shrink press fitted or adhered with adhesive.

Referring now to FIG. 5, the electrode actuation sleeve 32 has been retracted to the proximal position allowing the electrode arms 26 to expand outwardly for apposition with the vein wall to be treated. The distal ends 44 of the electrode arms 26 have withdrawn from the slots 46 in the distal tip somewhat although they are still contained therein. The stent arms 28 have not been expanded outwardly and are still in the fully contracted position. In this embodiment, the stent arms contract to a position that is less than the diameter of the catheter. However, this may not be required in other embodiments, although the stent arms 28 must contract to a position that is smaller than the final desired diameter of the vein to be treated so that the catheter can be removed.

Referring now to FIG. 6, both the electrode arms 26 and the stent arms 28 have been expanded to their fully expanded positions. The electrode actuation sleeve 30 has been slid proximally to release the electrodes 24 and the stent actuation sleeve has been slid to the full distal position where the inner stop tube 54 has contacted the stop surface 56.

One of the particular advantages of the invention is apparent by reference to FIG. 7. The catheter 20 has been advanced to a vein position just adjacent an incompetent valve 60, energy applied, and the vein shrunk until the valve 60 has resumed competency. Upon reaching the treatment site, the electrode actuation sleeve 32 was moved in the proximal direction. Because the electrode arms are biased outwardly by virtue of being pre-formed in a bow shape, they sprang into apposition with the vein wall. The stent arms 28 had also been expanded outwardly to the desired final diameter of the vein 10 and are shown at that position in FIG. 7. Energy was applied to the vein wall by the electrodes and shrinkage of the vein wall resulted. As the wall shrunk, it applied force against the electrodes causing the electrode arms 26 to contract. Because the electrode arms 26 are mounted with their distal ends free to move, as shown in FIGS. 4, 5, and 6, the electrode arms freely contracted as the vein wall shrunk. Upon reaching the diameter set by the stent arms 28, the vein stopped shrinking and the electrode arms stopped contracting.

The position of the electrode arms 26 relative to the stent arms 28 may be altered to produce catheters having different operational characteristics. For example, in one configuration, the proximal ends 40 of the electrode arms 26 are attached to the support tube 42 such that each electrode arm proximal end 40 overlays a stent arm 28 proximal end 50. Similarly, the slots 46 are positioned within the distal tip 34 such that each electrode arm distal end 44 overlays a stent arm 28 distal end 48. When configured in this manner the electrode arms 26 substantially overlay the stent arms 28 as shown in FIG. 6a. When the vein wall shrinks toward the electrode arms 26 the electrode arms 26 collapse onto the stent arms 28. The outward bowing of the arms 26, 28 combines to provide increased strength to stop further shrinkage of the vein once the vein has come in contact with the electrode arms.

In another configuration, the proximal ends 40 (FIGS. 4, 5, and 6) of the electrode arms 26 are attached to the support tube 42 such that each electrode arm proximal end 40 is positioned between adjacent stent arm 28 proximal ends 50. Similarly, the slots 46 are positioned within the distal tip 34 such that each electrode arm distal end 44 is positioned between adjacent stent arm distal ends 48. When configured in this manner the electrode arms 26 are interspaced between the stent arms 28 so that the electrode arms 26 can freely contract to the same diameter as the stent arms as shown in FIG. 6b. This configuration provides for a low-profile catheter having a small cross-sectional diameter which may be used to shrink small-diameter vessels.

In view of the above, it can be seen that precise control over the electrode arms 26 is not necessary. The electrode arms automatically expand into apposition with the vein treatment site and automatically contract as needed during vein shrinkage. Notably, the electrodes on the electrode arms automatically remain in contact with the shrinking vein wall during the entire shrinking process due to the outward bias on the electrode arms. Decoupling the stent arms from the electrode arms permits a more accurate selection of the final vein diameter in that the stent arms can be more precisely set at the desired diameter, locked in position, and not changed until after the procedure has been completed.

FIG. 8 presents a view of a system for delivering energy to biological tissue that incorporates aspects of the invention. The catheter 20 has a working end 22 with electrode arms 26 and stent arms 28 and includes a control handle 70 at its proximal end 72. The control handle has a first control switch 74 for moving the stent actuation sleeve 30 and a second control switch 76 for moving the electrode actuation sleeve 32. The control switches may each comprise a switch, lever, threaded control knob, or other suitable mechanism. In the case of the stent control switch, a locking mechanism is be provided (not shown), which may take the form of a higher friction sliding switch 74. Additionally, gradations 84 or other indications of the diameter of the stent arms are provided at the control handle 70 so that the stent arms may be set precisely by mere reference to handle indications. A guide wire port or fluid port 78 is also included at the proximal end.

An RF power generator 80 is connected to the proximal end of the catheter 20 and a processor 82 is connected with the RF generator. Although shown as being separate in FIG. 8, the processor 82 may form part of the RF generator and may be disposed in the same case. The RF generator electrically connected to the electrodes 24 is activated to provide suitable RF energy, preferably at a selected frequency from a range of 250 kHz to 350 MHZ. Suitable frequencies include 460 KHz and 510 KHz. One criterion used in selecting the frequency of the energy to be applied is the ability to filter the RF signal from temperature sensing means. Although not shown, one or more of the electrodes 24 in the figures may include a temperature sensor which may comprise a thermocouple. In such an embodiment, the selection of the RF frequency for compatibility with filter circuits for eliminating RF noise from thermocouple signals is important. Additionally, the processor 82 would receive the thermocouple signals and control the RF generator 80 in accordance with the temperature sensed by the thermocouples.

Figure 9:
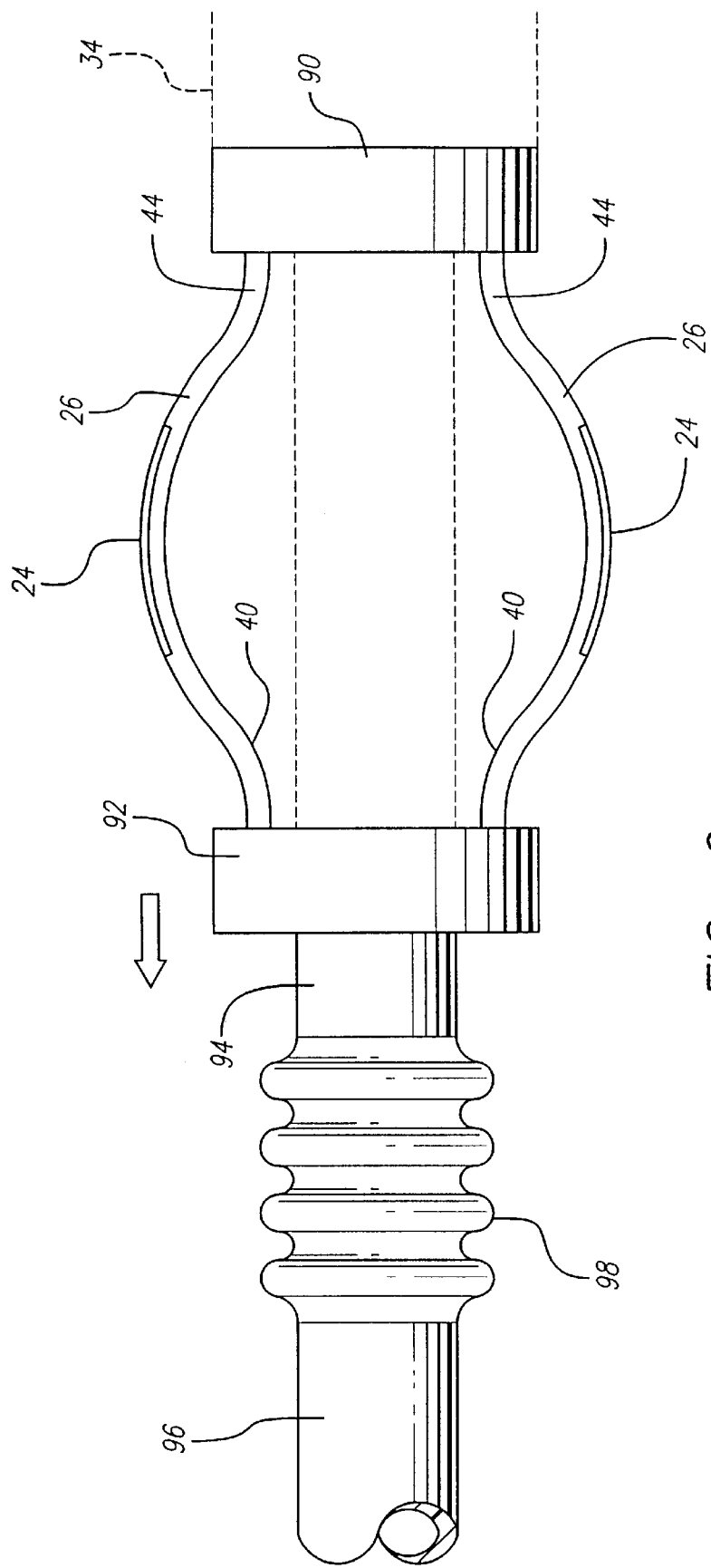
FIG. 9 is a view of an alternate embodiment of an electrode arm expansion control arrangement with a slidable control sleeve and bellows; the details of the stent arms are not shown so as to give the figure more clarity; however, the stent arms may be mounted as shown in FIGS. 5 and 6.

Referring now to FIG. 9, an alternate arrangement for expanding and contracting the electrode arms is shown. The details of the stent arms 28 are not shown so as to give the figure more clarity; however, the stent arms may be mounted as shown in FIGS. 5 and 6. In the arrangement of FIG. 9, the electrode arms 26 are pre-shaped in an outwardly bowed configuration and are firmly attached at their distal ends 44 to a mounting sleeve 90 located at the distal end of the catheter 20. The proximal ends 40 of the electrode arms are also firmly attached to a proximal mounting sleeve 92. The proximal mounting sleeve 92 is mounted to a slidable shaft 94 that is connected to an actuation sleeve 96 through a bellows 98. To keep the electrode arms in a contracted position, the electrode actuation sleeve 96 is pulled and locked in position.

When required, the electrode arms are expanded by releasing the electrode actuation sleeve 96 so that the bias on the electrode arms, caused by pre-forming them as discussed above, will cause them to bow outwardly until the electrodes 24 are in apposition with the vein wall. The actuation sleeve 96 is allowed to "float." As the vein wall shrinks, it applies contracting force against the electrode arms which tends to contract them. As the electrode arms contract, their proximal ends move the proximal mounting sleeve 92 and slidable shaft 94 in the proximal direction. Should the electrode actuation sleeve 96 not move freely for any reason, the bellows 98 will permit the electrode arms 26 to contract, as well as provide a barrier against fluid leakage into the catheter past the moving parts.

Figure 10:
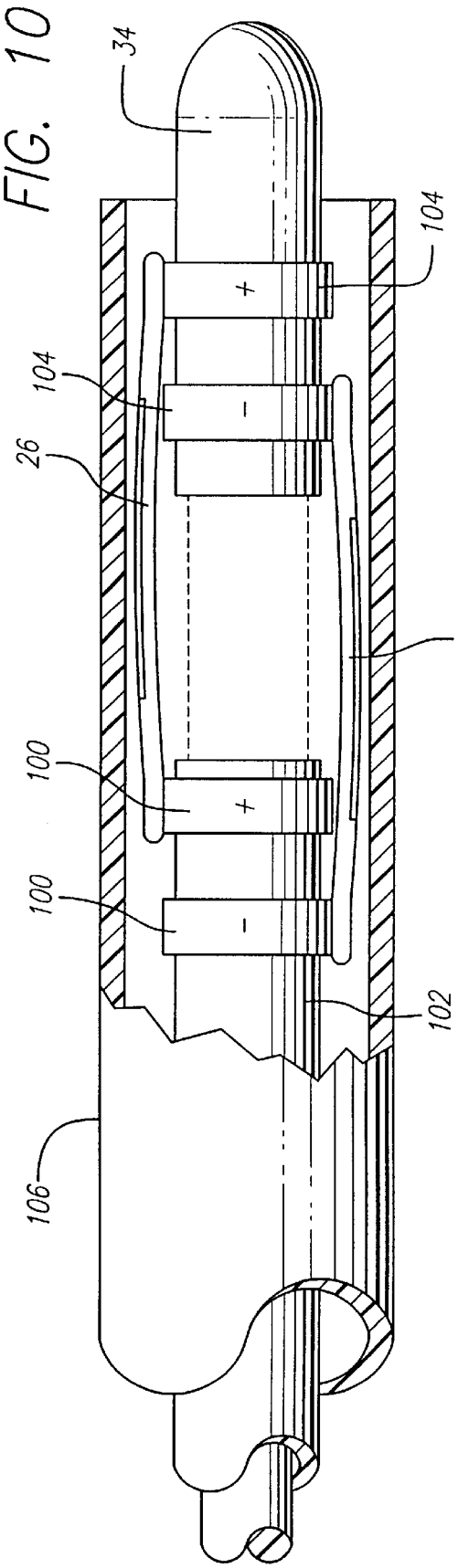
FIG. 10 is a view of an alternate embodiment of an electrode arm expansion arrangement having a pair of movable rings which allow for the expansion and contraction of the electrode arms, the electrode arms are shown in a contracted state; the details of the stent arms are not shown so as to give the figure more clarity; however, the stent arms may be mounted as shown in FIGS. 5 and 6.
Figure 11:
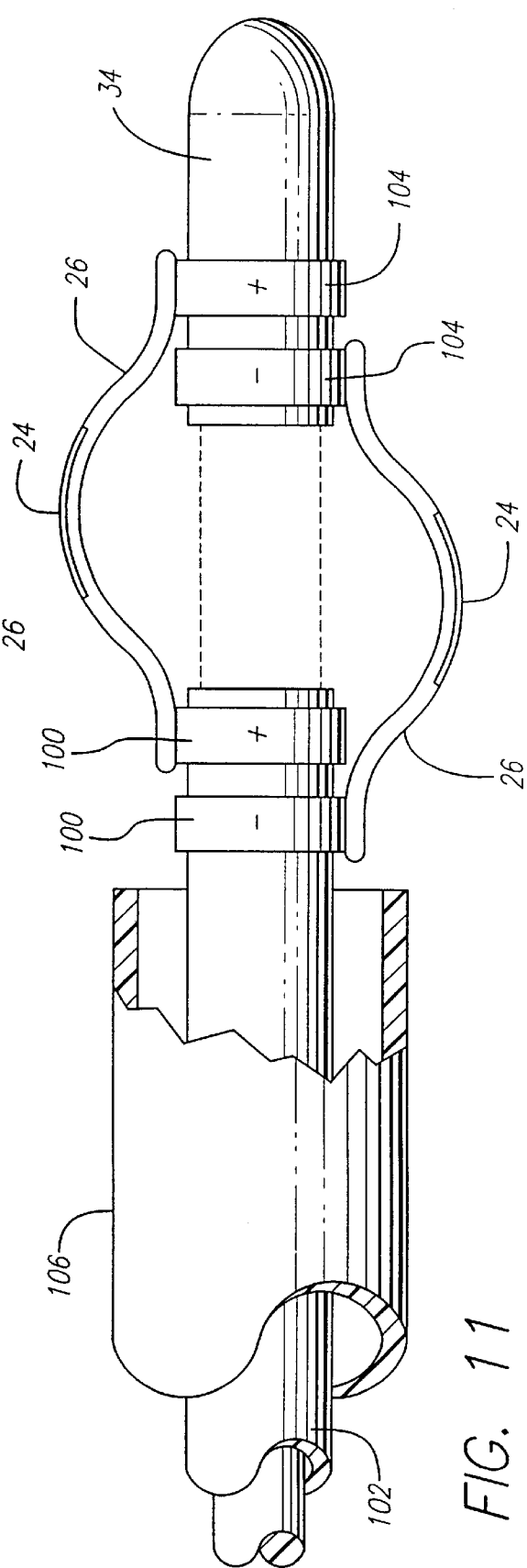
FIG. 11 is a view of the alternate embodiment of FIG. 10 showing the electrode arms in an expanded state.

Referring now to FIGS. 10 and 11, another alternate arrangement for expanding and contracting the electrode arms 26 is shown. Again, the details of the stent arms 28 are not shown so as to give the figure more clarity; however, the stent arms may be mounted as shown in FIGS. 5 and 6. In the arrangement of FIGS. 10 and 11, the electrode arms 26 are pre-shaped in an outwardly bowed configuration and attached at the proximal ends to fixed rings 100 that are firmly attached to a catheter shaft 102. At their distal ends the electrode arms 26 are mounted to floating rings 104 that can slide along the axis of the catheter shaft 102. Both the fixed rings 100 and floating rings 104 are electrically charged. The bowed electrode arms 26 are maintained in a contracted state by a restraining sleeve 106.

When required, the electrode arms 26 are expanded by retracting the restraining sleeve 106. The floating rings 104 slide over the catheter shaft 102 toward the fixed rings 100 as the electrode arms 26 bow outwardly until the electrodes 24 are in apposition with the vein wall. As the vein wall shrinks, it applies contracting force against the electrode arms which tends to contract the arms causing the floating rings 104 to slide away from the fixed rings 100.

In the arrangement just described the fixed rings 100 are located towards the proximal end of the catheter shaft 102 while the floating rings 104 are located towards the distal end. Alternatively, the fixed rings 100 may be placed towards the distal end of the catheter shaft 102 while the floating rings 104 are towards the proximal end.

Another embodiment of a catheter device having expandable electrode arms and stent devices is shown in FIGS. 12 and 13. This embodiment is similar to that shown in FIGS. 10 and 11 except that the electrode arms 26 in FIGS. 12 and 13 are not attached to the distal end of the catheter and are free-floating. The electrodes 24 on those arms 26 extend to the ends. Although the electrode portion 24 appears to encompass part of the side of the arm 26 in FIGS. 10 through 13, this is for purposes of illustration. In another embodiment, the electrode portion may only be located on the outward surface of the arm, as discussed previously.

Because the electrode arms 26 are anchored or attached to the catheter at their proximal ends and the restraining sleeve 106 slides distally to restrain the arms 26, the free floating configuration of the electrode arms 26 does not present a problem in releasing the arms to bow outwardly or in restraining them when withdrawing the catheter from the patient. The free floating configuration of the electrode arms 26 also results in ease of manufacturing as there are fewer connections to be made in assembling the catheter.

When treating the veins of the lower limbs, the patient is typically placed onto a procedure table with the feet dependent in order to fill the veins of the leg. The leg of the patient is prepped with antiseptic solution. A percutaneous introducer is inserted into the vein using a common Seldinger technique to access the saphenous or deep vein system. Alternatively, a venous cut-down can be used to access the vein system to be treated. The procedure for the repair of incompetent veins can be accomplished by a qualified physician with or without fluoroscopic or ultrasonic observation, or under direct visualization. Further, the physician could palpate the treatment area to determine the location of the catheter, and the treatment site, during the procedure when treating the superficial venous system.

The catheter 20 may be passed within the vein 10 after insertion through the skin. Alternatively, the guide wire 38 for the catheter 20 may be inserted into the vein. The guide wire 38 is advanced antegrade to the level of the most proximal incompetent vein valve which is to be repaired. The catheter 20 is then advanced upon the guide wire 38 and is fed up the leg through the vein to the level of the dilated venous section to be treated. Fluoroscopy, ultrasound, or an angioscopic imaging technique is then used to direct the specific placement of the catheter and confirm the position within the vein. Contrast material can be injected through or around the catheter to identify the incompetent venous sections to be repaired. A retrograde venogram can be performed in some cases to better localize the treatment site and effect.

The catheter 20 may be fit through a suitably sized sheath for the procedure. For example, a seven French sheath, which has about a 2.3 mm diameter, may be used. The sheath is composed of a biocompatible material with a low coefficient of friction.

Typically, the polarity of RF energy applied to adjacent electrodes is different to achieve a bipolar arrangement. In this arrangement the flow of electrical flux is substantially limited to the region between the electrodes and thus the spread of heat within the vein wall is similarly limited. However, a monopolar arrangement can also be used if desired.

RF energy is applied to the vein wall and that energy is converted within the adjacent venous tissue into heat. This thermal effect causes the venous tissue to shrink. The shrinkage is due to structural transfiguration of the collagen fibers in the vein. The collagen fibrils shorten and thicken in cross-section in response to the heat from the thermal effect. Although the collagen becomes more compacted during this process, it still retains elasticity. A tourniquet is applied to the vein to slow or stop venous blood flow during RF heating. For example, when treating a leg, a tourniquet is applied below the treatment site to slow or stop the antegrade flow of blood. This allows for more uniform heating and shrinking of venous tissue without any impact from a variable rate of blood flow that can cool the venous tissue. When RF energy is applied to the venous tissue at and around the incompetent valve of the dilated vein, the shrinkage of the venous tissue at the commissures can restore valvular competency by reducing the dilation which is preventing the proper functioning of the venous valve. Gross shrinkage of the vein diameter or shrinkage of the venous tissue can restore competency to the venous valve, by bringing valve leaflets closer together. If Doppler measurements of venous reflux show that the valve remains incompetent after the vein diameter is reduced, additional shrinkage can be performed adjacent and at the valve site. Shrinking the venous tissue and valve leaflet tissue in and around the venous valve restores valve competency.

RF energy is no longer applied after there has been sufficient shrinkage of the vein to alleviate the dilation of the vein near the valves, so as to restore venous function or valvular competency. Sufficient shrinkage can be detected by fluoroscopy, external ultrasound scanning, intravascular ultrasound scanning, direct visualization using an angioscope, or any other suitable method. For example, the catheter 20 can be configured to deliver an x-ray contrast medium to allow visualization by fluoroscopy for assessing the condition of the vein and the relationship of the catheter to the treatment area of the vein during the shrinkage process. As an alternative to fluoroscopy, external ultrasound techniques such as B-scanning using distinct ultrasound signals from different angles, or intravascular ultrasound can be used to acquire a more multidimensional view of the vein shrinkage at the treatment site. An angioscope can also be used to directly visualize and determine the extent and degree of vein shrinkage. Doppler ultrasound measurements are used to evaluate vein valve competence.

Substantial shrinkage may occur very rapidly, depending upon the specific treatment conditions. Because the shrinkage can proceed at a rather rapid rate, the RF energy is preferably applied at low power levels. The properties of the treatment site, such as temperature, can be monitored to provide feedback control for the RF energy. Other techniques such as impedance monitoring, and ultrasonic pulse echoing, can be utilized in an automated system which shuts down the application of RF energy from the electrodes 24 to the venous section when sufficient shrinkage of the vein is detected and to avoid overheating or coagulation in the vein. Monitoring these values in an automatic feedback control system for the RF energy can also be used to control the spread, including the depth, of the heating effect. The catheters are designed to use bipolar RF energy delivery to also limit the depth and spread of heating effects. In all instances, the application of RF energy is controlled so as to shrink the venous tissue sufficiently to restore the competency of the venous valve.

After treating the first venous section shown, the catheter 20 can be moved to the next venous valve displaying incompetence. The catheter 20 can be repositioned to treat as many venous sections and valves as necessary. RF energy is applied to each venous section to be repaired, until all of the desired venous sections are repaired and the valves are rendered competent. Multiple incompetent valves and dilated venous sections can be treated and repaired in a single minimally invasive procedure. If desired, a second introducer can be inserted into the limb of a patient in order to access either the deep or the superficial vein system, whichever has yet to be treated. The catheter can then be used to treat incompetent venous sections in the other vein system.

Where the catheter includes a fluid delivery lumen, such as a guide wire lumen through which anticoagulents may be introduced, anticoagulents such as heparinized saline or heparinized water can be delivered to the bloodstream during RF heating of the vein being treated. The delivered fluid reduces heating-induced coagulation of the blood. The fluid may also be delivered through ports formed along the side of the catheter near the working end and the electrodes (not shown).

After completing the RF procedure for each selected venous section, the catheter and electrodes are removed from the vasculature. The access point of the vein would be sutured closed if a cutdown had been performed, or local pressure would be applied after percutaneous sheath removal until bleeding was controlled. A bandage would then be applied. A pressure dressing may be necessary. Elastic pressure gradient stockings may be worn subsequently.

As an alternative to the antegrade approach, the catheter 20 can deliver the electrodes 24 to the venous treatment site from a retrograde approach. The catheter 20 is introduced into a percutaneous sheath that has been inserted through the skin and into the vein in a retrograde direction. The electrodes 24 at the working end 22 of the catheter 20 are advanced until contact with the cusp of the venous valve is observed by fluoroscopy, ultrasound, or other detection method. The catheter 20 is then pulled back slightly to allow treatment of the dilated valve sinus or leaflets in the vein. Placing the electrodes 24 in close apposition to the venous valve to cause local or preferential shrinkage near the valve can remedy separation of the commissures from vein dilation and restore venous function and valvular competency.

As can be readily ascertained from the disclosure herein, the surgical procedure of the present invention is accomplished without the need for prolonged hospitalization or post-operative recovery. The restoration of venous function is possible without the need for continued lifestyle changes, such as frequent leg elevation, the wearing of elastic support stockings, or prolonged treatment of recurrent venous stasis ulcers. When the saphenous veins are treated with the present invention, the patient can avoid vein stripping or phlebectomy surgery, thereby saving these veins for future use in bypass surgery. Moreover, the need for surgery of the arm and leg for transplantation of arm veins into the leg would not be necessary.

Early treatment of venous disease could prevent more serious complications such as ulceration, and valve damage caused by thrombophlebitis or thromboembolism. The cost of treatment and complications due to venous disease would be significantly reduced. There would be no need for extensive hospitalization for this procedure, and the need for subsequent treatment and hospitalization would also be reduced from what is currently needed. Furthermore, the minimally invasive nature of the disclosed methods would allow the medical practitioner to repair or treat several vein sections in a single procedure in a relatively short period of time.

It is to be understood that the type and dimensions of the catheter and electrodes may be selected according to the size of the vein to be treated. Although the present invention has been described as treating venous insufficiency of the lower limb such as varicose veins in the leg, the present invention can be used to intraluminally treat venous insufficiency in other areas of the body. For example, hemorrhoids may be characterized as outpocketed varicose veins in the anal region. Traditional treatments include invasive surgery, elastic ring ligation, and the application of topical ointments. Shrinking the dilated veins using RF energy can be accomplished in accordance with the present invention. Specifically, the catheter and electrode combination is introduced into the venous system, into the external iliac vein, the internal iliac vein, then either the hemorrhoidal or the pudendal vein. The catheter then delivers the electrode to the site of the dilated hemorrhoidal vein by this transvenous approach. Fluoroscopic techniques or any other suitable technique such as pulse-echo ultrasound, as previously discussed, can be used to properly position the electrode at the venous treatment site. The treatment site is preferably selected to be approximately two or more centimeters above the dentate line to minimize pain. The electrodes apply bipolar RF energy at a suitable frequency to heat shrink collagen in the vein wall for a sufficient amount of time to shrink, stiffen, and fixate the vein, yet maintain venous function or valvular competency. This intraluminal approach avoids the risks and morbidity associated with more invasive surgical techniques such as hemorrhoidectomy, while significantly reducing reflux of blood in the area without removing the venous tissue.

Another area of venous insufficiency relates to erectile impotency of the penis. A significant number of all physically-induced cases of impotence result from excessive drainage of blood from the penile venous system. Venous-drainage-impotence can be treated using the present invention. Catheters having a sufficiently small diameter can be used to deliver the electrodes through the dorsal vein of the penile venous system to shrink this venous outflow path. Fluoroscopic or ultrasound techniques can be used to properly position the electrode within the incompetent vein. RF energy or other radiant energy is applied from the electrodes at a suitable frequency to shrink the surrounding venous tissue in order to reduce the excessive amount of drainage from the penis while maintaining venous function or valvular competency. The amount of shrinkage of the vein can be limited by the diameter of the catheter itself, or the catheter or electrodes themselves can be expanded to the appropriate size. Ligation of these veins should be avoided so as to allow for the proper drainage of blood from an engorged penis which is necessary for proper penile function.

Another area of venous insufficiency suitable for treatment in accordance with the present invention involves esophageal varices. Varicose veins called esophageal varices can form in the venous system along the submucosa of the lower esophagus, and bleeding can occur from the swollen veins. Properly sized catheters can be used in accordance with the present invention to deliver the electrodes to the site of venous insufficiency along the esophageal varices. Endovascular access for the catheter is preferably provided through the superior mesenteric vein or portal vein to shrink the portal vein branches leading to the lower esophagus. Proper positioning of the electrode within the vein can be confirmed using fluoroscopic or ultrasound techniques. The electrodes apply RF energy or other radiant energy at a suitable frequency to shrink the vein and reduce the swelling and transmission of high portal venous pressure to the veins surrounding the esophagus.

Although described as applying RF energy from the electrodes, it is to be understood that other forms of energy such as microwaves, ultrasound, lower frequency electrical energy, direct current, circulating heated fluid, radiant light, and lasers may be used, and that the thermal energy generated from a resistive coil or curie point element may be used as well.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. A method of applying energy to selected biological tissue to shrink the tissue to a predetermined diameter, the method comprising the steps of:

introducing a catheter into the biological tissue;

expanding an adjustable stent device from the catheter to the predetermined diameter;

expanding an energy application device from the catheter to impart energy to the tissue;

applying energy to the tissue from the energy application device to cause shrinkage of the tissue to the stent device;

contracting the energy application device with the shrinking tissue so that energy is substantially continuously imparted to the tissue as the tissue shrinks; and ceasing the application of energy to the tissue when the tissue has shrunk in diameter such that it is in contact with the stent device.

2. The method of claim 1 wherein the step of expanding an adjustable stent device from the catheter to the predetermined diameter comprises the steps of:

expanding a plurality of stent arms outwardly to the predetermined diameter; and securing the stent arms in the expanded position thereby providing a mechanical stop surface against further tissue shrinkage.

3. The method of claim 2 wherein the step of expanding an energy application device from the catheter to impart energy to the tissue and the step of contracting the energy application device with the shrinking tissue comprise the steps of:

releasing a plurality of electrode arms that have been pre-formed into a bowed shape to expand outwardly into apposition with the biological tissue;

allowing one end of the electrode arms to move as the tissue shrinks and applies contracting force against the electrode arms so that the tissue may shrink to the predetermined diameter provided by the stent arms.

4. The method of claim 3 further comprising the step of overlying each stent arm with an electrode arm.

5. The method of claim 3 further comprising the step of interspacing the stent arms with the electrode arms.

6. The method of claim 3 wherein the step of allowing one end of the electrode arms to move as the tissue shrinks comprises the step of mounting the electrodes in a cantilever fashion so that one end is free to move as the tissue shrinks.

7. The method of claim 3 wherein the step of releasing a plurality of electrode arms to expand outwardly into apposition with the biological tissue comprises the step of releasing a plurality of electrode arms each having an electrode with a rounded shape to expand outwardly into apposition with the biological tissue.

8. The method of claim 3 wherein the step of releasing a plurality of electrode arms comprises the step of sliding a sleeve from a position in which it covers the electrode arms and confines them to a contracted position to a position where the electrode arms are uncovered.

9. The method of claim 8 wherein the step of sliding the sleeve comprises the step of pulling the sleeve towards the proximal end of the catheter.

10. The method of claim 1 further comprising the step of indicating the position of the expandable stent devices at the handle of the catheter.

11. The method of claim 1 comprising the step of inserting the catheter into a vein lumen.

12. The method of claim 11 further comprising the step of limiting fluid flow in the vein by applying a tourniquet.

* * * * *